(12) United States Patent
Matsuo et al.

(10) Patent No.: US 6,632,948 B2
(45) Date of Patent: Oct. 14, 2003

(54) AZETIDINE DERIVATIVE AND PROCESS FOR PREPARATION THEREOF

(75) Inventors: Kazuhiko Matsuo, Hyogo (JP); Kentaro Tsukuya, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/926,770

(22) PCT Filed: Apr. 18, 2001

(86) PCT No.: PCT/JP01/03323
§ 371 (c)(1),
(2), (4) Date: May 9, 2002

(87) PCT Pub. No.: WO01/79208
PCT Pub. Date: Oct. 25, 2001

(65) Prior Publication Data
US 2002/0151721 A1 Oct. 17, 2002

(30) Foreign Application Priority Data
Apr. 19, 2000 (JP) ........................................ 2000-117420

(51) Int. Cl.$^7$ ............................................. C07D 263/58
(52) U.S. Cl. ...................................................... 548/221
(58) Field of Search .......................................... 548/221

(56) References Cited

U.S. PATENT DOCUMENTS 5,650,521 A    7/1997   Jackson ....................... 548/556

FOREIGN PATENT DOCUMENTS

| EP | 0 542 525 A2 | 11/1992 |
|---|---|---|
| EP | 0 992 491 A1 | 10/1998 |
| EP | 0 974 670 A2 | 1/2000 |
| JP | 44-31574 | 12/1969 |
| WO | WO 91/07976 | 6/1991 |
| WO | WO 96/03374 | 2/1996 |
| WO | WO 99/03467 | 1/1999 |

OTHER PUBLICATIONS

David J. Mathre et al., "A Practical Enantioselective Synthesis of α,α–Diaryl–2–Pyrrolidinemethanol. Preparation and Chemistry of the Corresponding Oxazaborolidines"—*J. Org. Chem.* 1991, 56, 751–762.

Mohamad D. Shalati, et al., "Attempted Polymerization of Substituted Pipecolic Acid NCA's: Dimerization and Mechanism—*Department of Chemistry and the Macromolecular Research center, The University of Michigan.*" Journal of Polymer Science: Polymer Chemistry Edition, vol. 22, 107–120 (1984).

*Primary Examiner*—Mark L. Berch
*Assistant Examiner*—Kahsay Habte
(74) *Attorney, Agent, or Firm*—Armstrong, Westerman & Hattori, LLP

(57) ABSTRACT

Novel optically active or racemic azethidine carboxylic acid derivatives (azethidine-2-carboxylic acid N-carboxyamino acid anhydrides) which are useful as drug intermediates and an industrially advantageous process for producing the same are provided. Namely, a process for obtaining azethidine-2-carboxylic acid N-carboxyamino acid anhydrides starting with azethidine-2-carboxylic acids is provided. Via the azethidine-2-carboxylic acid N-carboxyamino acid anhydrides according to the invention, azethidine derivatives having peptide bond, which are useful as drugs, can be obtained by an industrial and economic process without resorting deblocking reaction.

6 Claims, No Drawings

AZETIDINE DERIVATIVE AND PROCESS FOR PREPARATION THEREOF

TECHNICAL FIELD

This invention relates to novel azethidine derivatives and a process for producing these compounds from azethidine-2-carboxylic acids. More particularly, it relates to azethidine-2-carboxylic acid N-carboxyamino acid anhydrides represented by the following formula (1):

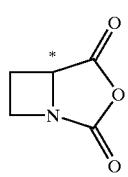

(1)

and a process for producing these compounds from azethidine-2-carboxylic acids represented by the following formula (4):

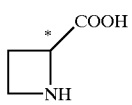

(4)

The azethidine-2-carboxylic acid N-carboxyamino acid anhydrides represented by the formula (1) are useful compounds as intermediates of drugs and the like.

BACKGROUND ART

The azethidine-2-carboxylic acid N-carboxyamino acid anhydrides represented by the formula (1) are novel compounds and no prior art has been reported hitherto concerning any processes for producing these compounds. Azethidine derivatives having peptide bond, which have a thrombin inhibitory activity, are highly useful as drug intermediates (U.S. Pat. No. 5, 714,485 and WO98/50420). These drug intermediates can be produced starting with (S)-azethidine-2-carboxylic acid which can be prepared by a publicly known method. However, condensation of an azethidine-2-carboxylic acid with an amine can be hardly performed in a single step in general. Namely, it is needed that the amine moiety of the azethidine-2-carboxylic acid is protected with a carbamate protective group, etc. followed by the condensation with the use of a condensing agent such as 1,3-dicyclohexylcarbodiimide (DCCD) and deblocking of the N-protective group. Therefore, it has been required to develop a more convenient production process.

DISCLOSURE OF THE INVENTION

This invention provides intermediate compounds useful in producing drugs, in particular, azethidine derivatives having peptide bond and a process for producing the same. Under the above-described conditions, the inventors have conducted intensive studies. As a result, they have found out that the azethidine derivatives having peptide bond can be efficiently produced via azethidine-2-carboxylic acid N-carboxyamino acid anhydrides, which are novel compounds, without resort to the deblocking procedure. The invention has been completed based on this finding.

Accordingly, the invention provides optically active azethidine-2-carboxylic acid N-carboxyamino acid anhydrides and racemate thereof, which are useful in producing azethidine derivatives having peptide bond, and a process whereby these compounds can be efficiently and economically produced on an industrial scale.

BEST MODE FOR CARRYING OUT THE INVENTION

The optically active azethidine-2-carboxylic acid N-carboxyamino acid anhydrides and racemate thereof provided by the invention are compounds represented by the following formula (1):

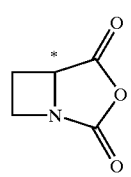

(1)

The term "optically active compound" as used herein means one of the (S)- and (R)-enantiomers alone of an azethidine-2-carboxylic acid N-carboxyamino acid anhydride or a mixture of these enantiomers containing one of them at a higher mixing ratio. On the other hand, the term "racemate" as used herein means a mixture containing the (S)- and (R)-enantiomers in the same amounts.

Next, the process for producing an azethidine-2-carboxylic acid N-carboxyamino acid anhydride will be described.

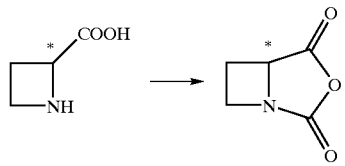

An azethidine-2-carboxylic acid to be used as the starting material in the invention can be produced by, for example, the process described in WO98/47867.

An azethidine-2-carboxylic acid N-carboxyamino acid anhydride can be easily produced by reacting an azethidine-2-carboxylic acid with phosgene, di-phosgene and/or tri-phosgene.

Phosgene is used in an amount of generally from 0.1 to 10 mole equivalents, preferably from 1 to 5 mole equivalents, as much as the azethidine-2-carboxylic acid. Di-phosgene is used in an amount of generally from 0.1 to 10 mole equivalents, preferably from 0.5 to 5 mole equivalents, as much as the azethidine-2-carboxylic acid. Tri-phosgene is used in an amount of generally from 0.1 to 10 mole equivalents, preferably from 0.3 to 5 mole equivalents, as much as the azethidine-2-carboxylic acid.

Although the reaction may be carried out without using any solvents, it is usually performed in an organic solvent. Examples of the solvent, in case of using, involve ether solvents such as diethyl ether, diisopropyl ether, tetrahydrofuran, 1,4-dioxane and tertiary-butyl ethyl ether; ester solvents such as ethyl acetate, methyl acetate, propyl acetate and methyl propionate; hydrocarbon solvents such as pentane, hexane, heptane, cyclohexane, petroleum ether, toluene, benzene and xylene; nitrile solvents such as acetonitrile and propionitrile; ketone solvents such as acetone and ethyl methyl ketone; amide solvents such as N,N-dimethylformamide and N,N-dimethylacetamide; sulfoxide solvents such as dimethyl sulfoxide; and halogenated hydrocarbon solvents such as methylene chloride, chloroform and carbon tetrachloride. Among all, ether solvents are preferable and tetrahydrofuran is most desirable. Either one of these solvents or a mixture of two or more thereof may be used. The solvent is usually employed in an amount of from 1 to 50% by weight, preferably from 5 to 30% by weight, based on the azethidine-2-carboxylic acid, though the invention is not restricted thereto.

The reaction temperature varies depending on the reactants and reaction solvent employed. Usually it ranges from −50 to 100° C., preferably from −10 to 80° C. and still preferably from 30 to 60° C.

The reaction time may be arbitrarily selected within a scope of usually from 0.5 to 10 hours, preferably from 2 to 7 hours and still preferably from 3 to 5 hours.

The compound (1) thus produced and its enantiomers can be collected as a compound having an arbitrarily high purity by optionally subjecting to publicly known separation and purification procedures such as concentration, extraction, chromatography and recrystallization.

The azethidine-2-carboxylic acid N-carboxyamino acid anhydrides produced by the process according to the invention can be easily introduced into azethidine derivatives (azethidine-2-carboxylic acid amides) having peptide bond by reacting with an amine. For example, (S)-azethidine-2-carboxylic acid (4-aminocyclohexyl) methanamide can be obtained by adding a THF solution containing (S)-azethidine-2-carboxylic acid N-carboxyamino acid anhydride to a liquid mixture of a 1 M sodium hydroxide solution containing (4-aminocyclohexyl)methanamine and tetrahydrofuran (THF) under ice-cooling followed by stirring.

EXAMPLE

To further illustrate the invention in greater detail, the following example will be given. However, it is to be understood that the invention is not construed as being restricted thereto.

EXAMPLE

Synthesis of Azethidine-2-carboxylic Acid N-carboxyamino Acid Anhydride

At room temperature, (S)-azethidine-2-carboxylic acid (1.0 g, 99.9% ee or higher) was suspended in 25 ml of tetrahydrofuran. Then tri-phosgene (1.0 g) was added thereto. The suspension was heated to 50° C. and stirred for 4 hours. After allowing to cool, the solvent was distilled off under reduced pressure to give a pale yellow oil (1.5 g).

$^1$HNMR(CDC13) δ 4.52 (dd, 1H), 3.76–3.62 (m, 2H), 2.44–2.36 (m, 1H), 2.23–2.14 (m, 1H), $^{13}$CNMR (CDC13) δ 169.10, 152.27, 55.44, 40.37, 34.22.

To confirm the optical purity, the azethidine-2-carboxylic acid N-carboxyamino acid anhydride thus formed was hydrolyzed into azethidine-2-carboxylic acid and then analyzed by HPLC. The (S)-azethidine-2-carboxylic acid thus obtained showed an optical purity of 99.9%ee or higher. Conditions for HPLC:

column Sumichiral: OA-6000 (Sumitomo Chemical Analysis Service) mobile phase: 2 mM aqueous solution of copper sulfate flow rate: 0.5 ml/min detection wavelength: 254 nm temperature: 30° C.

INDUSTRIAL APPLICABILITY

The invention provides novel azethidine-2-carboxylic acid N-carboxyamino acid anhydrides which are useful as drug intermediates and a process by which these compounds can be industrially advantageously produced.

What is claimed is:

1. An optically active or racemic azetidine-N,2-dicarboxylic acid anhydride represented by the following formula (1):

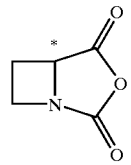

(1)

wherein * represents an asymmetric carbon.

2. (S)-azetidine-N,2-dicarboxylic acid anhydride represented by the following formula (2):

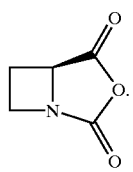

(2)

3. (R)-azetidine-N,2-dicarboxylic acid anhydride represented by the following formula (3):

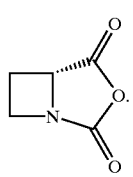

(3)

4. A process for producing an azetidine-N,2-dicarboxylic acid anhydride represented by the following formula (1):

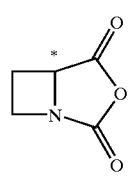

(1)

wherein * represents an asymmetric carbon;

from an azetidine-2-carboxylic acid represented by the following formula (4):

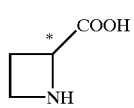

(4)

wherein * represents an asymmetric carbon, said process comprising the step of:
treating the azetidine-2-carboxylic acid with phosgene, di-phosgene and/or triphosgene.

5. The production process as claimed in claim 4, wherein:
said azetidine-2-carboxylic acid is (S)-azetidine-2-carboxylic acid and the product is (S)-azetidine-N,2-dicarboxylic acid anhydride.

6. The producing process as claimed in claim 4, wherein:
said azetidine-2-carboxylic acid is (R)-azetidine-2-carboxylic acid and the product is (R)-azetidine-N,2-dicarboxylic acid anhydride.

* * * * *